US009153226B2

(12) United States Patent
Wurm

(10) Patent No.: US 9,153,226 B2
(45) Date of Patent: Oct. 6, 2015

(54) ADAPTIVE NOISE CONTROL

(75) Inventor: Michael Wurm, Straubing (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 743 days.

(21) Appl. No.: 13/160,154

(22) Filed: Jun. 14, 2011

(65) Prior Publication Data

US 2011/0305347 A1 Dec. 15, 2011

(30) Foreign Application Priority Data

Jun. 14, 2010 (EP) .................................... 10165787

(51) Int. Cl.
*A61F 11/06* (2006.01)
*G10K 11/178* (2006.01)
*H04B 15/00* (2006.01)

(52) U.S. Cl.
CPC .................................... *G10K 11/178* (2013.01)

(58) Field of Classification Search
CPC ............ G10K 11/178; G10K 11/1786; G10K 2210/108; G10K 2210/503; H04R 3/005; H04R 25/407; G10L 21/0208; G10L 2021/02165
USPC ............ 381/71, 71.11, 94.1–94.9, 71.2–71.8
See application file for complete search history.

(56) References Cited

U.S. PATENT DOCUMENTS 5,278,913 A 1/1994 Delfosse et al.
7,110,554 B2 * 9/2006 Brennan et al. .............. 381/94.7
2003/0219131 A1 11/2003 Akiho
2004/0037431 A1 2/2004 Vaishya
2005/0207585 A1 * 9/2005 Christoph ................. 381/71.11

FOREIGN PATENT DOCUMENTS

JP 03203493 9/1991
JP 07199967 8/1995

(Continued)

OTHER PUBLICATIONS

Rees et al., "Adaptive Algorithms for Active Sound-Profiling", IEEE Transactions on Audio, Speech, and Language Processing, vol. 14, No. 2, Mar. 2003, pp. 733-719.

(Continued)

*Primary Examiner* — Vivian Chin
*Assistant Examiner* — Ammar Hamid
(74) *Attorney, Agent, or Firm* — O'Shea Getz P.C.

(57) ABSTRACT

Adaptive noise control for reducing power of an acoustic noise signal radiated from a noise source to a listening position comprises providing an electrical reference signal correlated with the acoustic noise signal; filtering the electrical reference signal with an adaptive filter to provide an electrical output signal; multiplying the electrical output signal of the adaptive filter by a gain factor to provide a first electrical compensation signal; filtering and multiplying the electrical output signal of the adaptive filter by the inverse of the gain factor to provide a second electrical compensation signal, the second gain factor being equal to 1 subtracted by the first gain factor; radiating the first electrical compensation signal to the listening position with an acoustic transducer; sensing a residual electrical error signal at the listening position; adding the second electrical compensation signal to the electrical error signal to provide a compensated error signal; and adapting filter coefficients of the adaptive filter as a function of the compensated error signal and the reference signal.

14 Claims, 7 Drawing Sheets

(56) References Cited

FOREIGN PATENT DOCUMENTS

| | | |
|---|---|---|
| JP | 09171388 | 6/1997 |
| JP | 2001051703 | 2/2001 |
| JP | 2007212700 | 8/2007 |
| JP | 2007243739 | 9/2007 |

OTHER PUBLICATIONS

Kuo et al., "Development and Analysis of an Adaptive Noise Equalizer", IEEE Transactions on Speech and Audio Processing, vol. 3, No. 3, May 1995, pp. 217-222.

* cited by examiner

ADAPTIVE NOISE CONTROL

CLAIM OF PRIORITY

This patent application claims priority from EP Application No. 10 165 787.2 filed Jun. 14, 2010, which is hereby incorporated by reference.

FIELD OF TECHNOLOGY

The present invention relates to adaptive noise control in an audio signal processing system and in particular to controlling the cancellation performance both in amplitude and phase.

RELATED ART

A disturbing noise (also referred to as "noise" or "disturbing sound signals"), in contrast to a useful sound signal, is sound that is not intended to be heard or perceived, for example, by a listener. In a motor vehicle, disturbing noise may include sound signals generated by mechanical vibrations of an engine and/or components mechanically coupled thereto (e.g., a fan), wind passing over and around the vehicle, and/or tires contacting, for example, a paved surface. In particular for lower frequency ranges, noise control systems and methods are known that eliminate or at least reduce the noise radiated into a listening room using a destructive interference (i.e., by superposing the noise signal with a compensation signal). However, the feasibility of these systems and methods relies on the development of cost effective, high performance digital signal processors, which may be used together with an adequate number of suitable sensors and transducers.

Common, active noise suppressing or reducing systems also known as "active noise control" (ANC) systems generate a compensation sound signal having the same amplitude and the same frequency components as the noise signal to be suppressed. However, the compensation sound signal has 180° (one hundred eighty degree) phase shift with respect to the noise signal. As a result, the noise signal is eliminated or reduced, at least at certain locations within the listening room, due to the destructive interference between the compensation sound signal and the noise signal. "Listening room" in this context is the space in which the ANC exhibits its noise suppressive effect, e.g., the passenger compartment of a vehicle.

Modern active noise control systems implement digital signal processing and digital filtering techniques. Typically, a noise sensor (e.g., a microphone or a non-acoustical sensor) is used to provide an electrical reference signal representing the disturbing noise signal generated by a noise source. The reference signal is fed to an adaptive filter which supplies a filtered reference signal to an acoustic transducer (e.g., a loudspeaker). The acoustic transducer generates a compensation sound field having a phase opposite to that of the noise signal within a defined portion ("listening position") of the listening room. The compensation sound field interacts with the noise signal thereby eliminating or at least damping the noise within the listening position. The residual noise within the listening environment and/or the listening room may be sensed using a microphone. The resulting microphone output signal is used as an "error signal" and is provided to the adaptive filter, where the filter coefficients of the adaptive filter are modified such that a norm (e.g., the power) of the error signal and, thereby, the residual noise finally perceived by the listener is minimized.

All applicable algorithms provide compensation for the added physical plant between the output of the adaptive system and the sensed error signal. Known algorithms are, e.g., the filtered-x-LMS (FXLMS), filtered-error-LMS (FELMS) and modified-filtered-x-LMS (MFXLM).

A model that represents the acoustic transmission path (physical plant) from the acoustic transducer (i.e., loudspeaker) to the error signal sensor (i.e., microphone) is used for applying the FXLMS, FELMS, MFXLMS (or any related) algorithm. This acoustic transmission path from the loudspeaker to the microphone is usually referred to as a "secondary path" of the ANC system, whereas the acoustic transmission path from the noise source to the microphone is usually referred to as a "primary path" of the ANC system. The corresponding process for identifying the transmission function of the secondary path is referred to as "secondary path system identification".

The transmission function (i.e., the frequency response) of the secondary path system of the ANC system may have a considerable impact on the convergence behavior of an adaptive filter, and thus on the stability behavior thereof, and on the speed of the adaptation. The frequency response (i.e., magnitude response and/or phase response) of the secondary path system may be subject to variations during operation of the ANC system. A varying secondary path transmission function may have a negative impact on the performance of the active noise control, especially on the speed and the quality of the adaptation produced by the FXLMS, FELMS or MFXLMS algorithm. The negative impact is caused when the actual secondary path transmission function is subjected to variations and no longer matches an a priori identified secondary path transmission function that is used within the active noise control system. All these effects limit the achievable attenuation performance of an ANC system.

Further, in certain applications it is desired to control the level and phase of noise attenuation over frequency.

There is a general need for adaptive noise control with selectable cancellation characteristics while maintaining speed and quality of adaption as well as robustness of the adaptive noise control.

SUMMARY OF THE INVENTION

According to one aspect of the invention, an adaptive noise control system is disclosed for reducing, at a listening position, power of an acoustic noise signal radiated from a noise source to the listening position. The system includes an adaptive filter that receives an electrical reference signal representing the acoustic noise signal and an electrical error signal representing the acoustic signal at the listening position and that provides an electrical output signal; a signal processing arrangement that is connected downstream of the adaptive filter and that provides a first electrical compensation signal indicative of the electrical output signal multiplied by a first gain factor and a second electrical compensation signal indicative of the electrical output signal multiplied by a second gain and filtered by an estimated transfer function of the secondary path, the second gain factor being equal to one subtracted by the first gain factor; the second compensation signal being added to the error signal for compensation; and at least one acoustic transducer that receives the first electrical compensation signal and radiates an acoustic compensation signal indicative of the first electrical compensation signal to the listening position.

According to another aspect of the invention, an adaptive noise control method is disclosed for reducing, at a listening position, power of an acoustic noise signal radiated from a noise source to the listening position. The method includes providing an electrical reference signal correlated with the acoustic noise signal; filtering the electrical reference signal with an adaptive filter to provide an electrical output signal; multiplying the electrical output signal of the adaptive filter by an adaptive first gain factor to provide a first electrical compensation signal; filtering and multiplying the electrical output signal of the adaptive filter by a second gain factor to provide a second electrical compensation signal, the second gain factor being equal to one subtracted by the first gain factor; radiating the first electrical compensation signal to the listening position with an acoustic transducer; sensing a residual electrical error signal at the listening position; adding the second electrical compensation signal to the electrical error signal to provide a compensated error signal; and adapting filter coefficients of the adaptive filter as a function of the compensated error signal and the reference signal.

DESCRIPTION OF THE DRAWINGS

The components in the drawings are not necessarily to scale; instead emphasis is placed upon illustrating the principles of the invention. Moreover, in the drawings, like reference numerals designate corresponding parts.

DETAILED DESCRIPTION OF THE INVENTION

Figure 1:
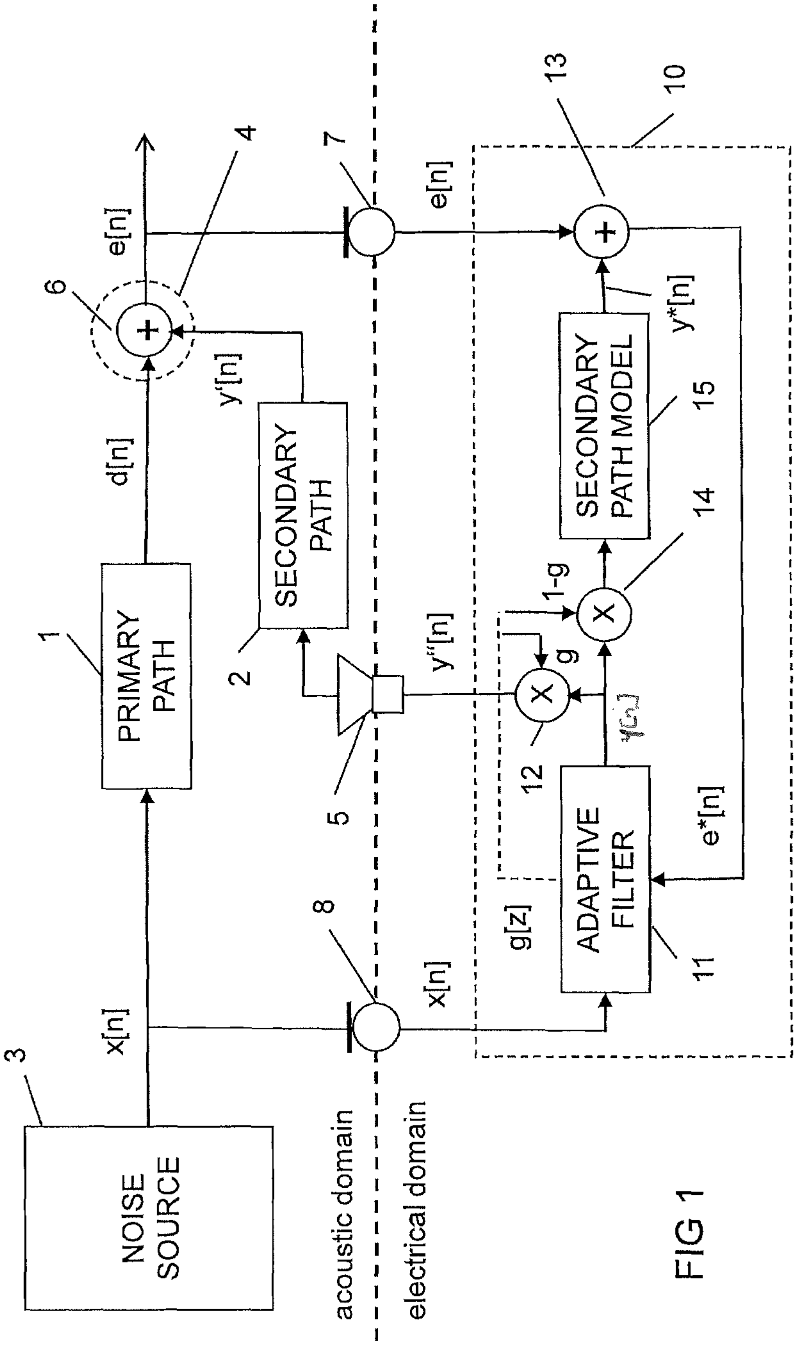
FIG. 1 is a block diagram illustration of a basic adaptive noise control system with controllable attenuation in time domain.

FIG. 1 illustrates the signal flow in a basic adaptive noise control system for generating a compensation signal that at least partially compensates for, eliminates or modifies an undesired disturbance signal d[n]. An acoustic noise signal x[n] (reference noise signal) representative of all disturbing noise that may occur is radiated via a primary path 1 from a noise source 3 to a listening position 4. The acoustic noise signal x[n] may include, for example, sound signals generated by mechanical vibrations of an engine, sound of components mechanically coupled thereto such as a fan, wind passing over and around the vehicle, and tires contacting a paved surface. For the sake of simplicity, all such sources of noise are represented herein by the noise source 3. The primary path 1 may impose a delay to the acoustic noise signal x[n], for example, due to the propagation of the disturbing noise from the noise source 3 to the listening position, i.e., a location in the listening room where a suppression of the disturbance noise d[n] signal should be achieved, to the desired "point of silence".

An acoustic compensation signal y"[n] is radiated from a transducer such as a loudspeaker 5 along a secondary path 2 to the listening position 4, appearing there as delayed compensation signal y'[n]. At the listening position 4, the disturbance noise signal d[n] and the delayed compensation signal y'[n] interfere with each other resulting in an acoustic error signal, herein referred to as error signal e[n]. The interaction of the disturbance noise signal d[n] and the delayed compensation signal y'[n] can be described as signal addition which is illustrated in FIG. 1 by an adder 6. The acoustic error signal e[n] is transferred by another transducer such as a microphone 7 into an electrical error signal which, for the sake of simplicity, is like the acoustic error signal herein also referred to as error signal e[n]. With still another transducer such as a microphone 8 the acoustical noise signal is picked up at the noise source 3 and transformed into an electrical noise signal. However, any other sensor may be used that generates a signal corresponding to the acoustical noise signal. As with the error signal e[n], the acoustic and the electrical noise signals are both simply referred to as noise signal x[n] hereinafter.

A signal processing arrangement 10 receives and processes the noise signal x[n] and the error signal e[n] to generate the compensation signal y"[n], which is the compensation signal y[n] multiplied in the time domain by a (first) gain factor g (in the present case a real number) in a multiplier 12. In the signal processing arrangement 10, the compensation signal y[n] is provided by an adaptive filter 11 that receives the noise signal x[n] and a modified error signal e*[n]. This modified error signal e*[n] is provided by an adder 13 that adds the error signal e[n] and a modified compensation signal y*[n]. This modified compensation signal y*[n] is the compensation signal y[n] multiplied in the time domain by (second) gain factor 1−g (the second gain factor is equal to 1 subtracted by the first gain factor) in a multiplier 14 and filtered by a filter that models the secondary path 2, hereinafter referred to as secondary path estimation filter 15. The multiplication by quantity "1−g" in the multiplier 14 compensates for the multiplication by "g" in the multiplier 12 (in connection with secondary path model established by the filter 15) to the effect that the modified error signal e*[n] is the same as error signal e[n] in a conventional ANC system, that is, when the multiplier 12 is bypassed and the multiplier 14 is omitted (g=1). Thus, the error signal provided to the adaptive filter is the same as in conventional ANC systems.

In the arrangement illustrated in FIG. 1, a signal (e.g., compensation signal y"[n]) which is correlated to the noise signal x[n] (also referred to as a "reference noise signal") is used for driving a compensation loudspeaker (e.g., loudspeaker 5). The "system response" to a noise input x[n] from the noise source 3 is represented by at least one microphone output signal (error signal e[n]) that is fed back via a control system to the compensation loudspeaker. The compensation loudspeaker generates "anti-noise" (e.g., compensation signal y'[n]) for suppressing the actual disturbance noise signal d[n] at the desired position. The adaptive filter 11 is updated to reduce the size of signal e*[n] for example in a least mean square sense by using a known adaption algorithm, e.g., LMS, NLMS, RLS etc. The effect of the gain factor "g" on the behavior of the system is described in more detail with reference to FIG. 2.

Figure 2:
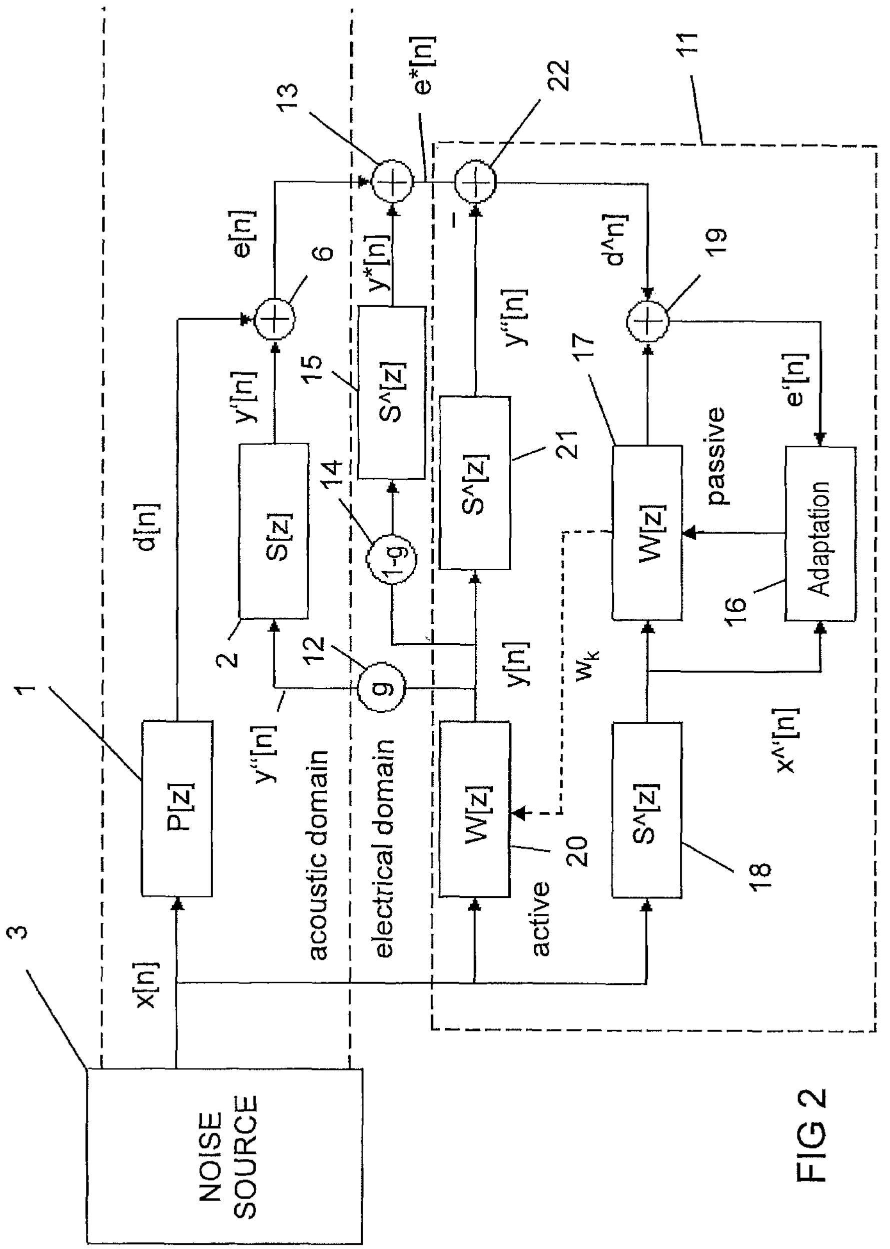
FIG. 2 is a block diagram illustration of a more specific embodiment of the basic adaptive noise control system shown in FIG. 1.

The block diagram of FIG. 2 illustrates a more specific embodiment of the basic adaptive noise control system shown in FIG. 1. The system illustrated in FIG. 2 includes the primary path 1, the secondary path 2, and the signal processing arrangement 10 shown in FIG. 1, e.g., a digital signal processor with adequate software implementation. The signal processing arrangement 10 shown in FIG. 1 includes the adaptive filter 11, the secondary path estimation filter 15, the adder 13 and the multipliers 12 and 14. The adaptive filter 11, as illustrated in more detail in FIG. 2, includes an adaptation unit 16 and a controllable filter 17 controlled by the adaptation unit 16. The adaptation unit 16 and the filter 17 are supplied with an output signal of a filter 18 which receives the reference noise signal x[n]. The output signal of filter 17 is added to the approximated disturbance noise signal d^[n] in an adder 19 that provides an modified error signal e'[n] to the adaptation unit 16. The coefficients $w_k$ are also copied into a filter 20 which, thus, has the transfer function W[z] as filter 17 does. It receives the reference noise signal x[n] and provides the compensation signal y[n] which is supplied to a filter 21 with the transfer function S^(z) (approximated secondary path) for providing the compensation signal y"[n]. The compensation signal y"[n] is subtracted from the error signal e*[n] in an adder 22 that provides as an output the signal d^[n]. This signal d^[n] is an estimation of the disturbance noise signal d[n] and is equal to disturbance noise signal d[n] when equality S^(z)=S(z) holds. In the frequency domain this can be easily verified according to the following by equation:

$$
\begin{aligned}
D^\wedge(z) &= D(z) + Y(z)\cdot(g\cdot S(z) + (1-g)\cdot S^\wedge(z) - S^\wedge(z))\\
&= D(z) + Y(z)\cdot G(z)\cdot(S(z) - S^\wedge(z))
\end{aligned}
$$

The primary path 1 has a transfer function P(z) representing the transfer characteristics of the signal path between the noise source 3 and the listening position 4. The secondary path 2 has a transfer function S(z) representing the transfer characteristics of the signal path between the loudspeaker 5 and the listening position 4. The filters 17 and 20 have the transfer function W(z) that is controlled by an optimized set of filter coefficients $w_k$ (=$w_0$, $w_1$, $w_2$, . . . $w_m$) provided by the adaptation unit 16. The transfer function S^(z) is an estimation of the secondary path transfer function S(z). The primary path 1 and the secondary path 2 are "real" systems representing the acoustical properties of the listening room, wherein the other transfer functions are implemented in the signal processing arrangement 11. The filter 20 is part of an active signal path, i.e., a path where the actual signal to be radiated by the loudspeaker 5 is processed. The filter 17 is part of a passive signal path, i.e., it is used for optimizing the filter coefficients $w_k$ in a kind of "background", "dummy" or "shadow" filter structure. This shadow structure of the system has to be found advantageous in practice for handling the stability of the system.

In the system illustrated in FIG. 2, the noise signal x[n] is used as "reference signal" for the adaptive filter 11. The noise signal x[n] is measured, for example, by an acoustic sensor such as a microphone or a non-acoustical sensor such as a revolution counter. When using a non-acoustical sensor, the derived signal may be post-processed by a synthesizer, special filter or the like. The adaptive filter 11 provides the compensation signal y[n] which is radiated after multiplication with gain g in multiplier 12 via the secondary path 2 to the listening position where it appears as the modified compensation signal y'[n]. This modified compensation signal y'[n] has an approximately 180 degree phase shift to that of the delayed reference noise signal x[n] and, thus, destructively superposes with the disturbance noise signal d[n] from the primary path 1. The "result" of the superposition is a measurable residual signal used as the error signal e[n]. After adding to error signal e[n] and the modified compensation signal y*[n] provided by the secondary path estimation filter 15, the resulting modified error signal e*[n] is input to the adaptive filter 11.

After successful adaption of transfer function W[z] the transfer function W(z)·S(z) resulting from the series connection of the filters 17 and 18 approaches the transfer function P(z) of the primary path 1 due to the adaptation process, wherein the output signal d[n] of the primary path 1 and the output signal y'[n] of the secondary path 2 superpose destructively thereby suppressing the effect of the input signal x[n] in the considered listening position. The error signal e'[n] and the filtered reference signal x^'[n] derived from the reference noise signal x[n] by filtering with the estimated secondary path transfer function S^(z) are supplied to the adaptation unit 16. The adaption unit 16 calculates, for example using an LMS algorithm, the filter coefficients $w_k$ for the filter 17 (and the filter 20) with the transfer function W(z) such that a norm of the error signal |e'[n]| or |e*[n]|, respectively, becomes relatively small, e.g., is minimized. The maximum achievable performance of this minimization depends, among others, on the characteristic of the secondary path, the quality of the secondary path in the model used, the type of adaption and the nature and characteristics of the underlying noise signal. In the special case "g=1" one can easily verify, that e*[n]=e[n] and the system will show its full maximal attenuation performance in the acoustic domain.

The adaptive filter 11 in the system of FIG. 2 includes an additional filter 20 with the transfer function W[z] and an additional filter 21 with the estimated secondary path transfer function S^[z]. The filter characteristic of the adaptive filter 20 upstream of the "real" secondary path 2 and the filter characteristic of the shadow filter 17 are identical and updated by the (LMS) adaptation unit 16. The filter 21 receives the compensation signal y[n] and provides an estimation of the secondary path output y"[n]. The difference between the modified compensation signal y"[n] and the error signal e*[n] provided by a microphone (not shown in FIG. 2 for the sake of simplicity) disposed in the location where noise cancellation is desired, i.e., the listening position 4 is provided by the summer 22. The resulting difference is an estimated signal d^[n] of the primary path output d[n]. The output signal of the (passive, i.e., not actively adapted) shadow filter 17, the compensation signal y"[n] is added to the estimated signal d^[n] to provide the modified error signal e'[n] used to update the filter coefficients $w_k$ of the filters 17 and 20. The filter 20 receives the reference noise x[n], whereas the shadow filter 17 and the LMS adaptation unit 16 receive the filtered reference noise signal x^'[n].

Assuming g=1, the path including the filter 21 is used to model the actual radiated acoustical compensation signal y"[n]. The adder 22 outputs an estimation of the acoustical disturbance noise signal d[n], i.e., the estimated disturbance noise signal d^[n] that depends on the quality of the transfer function S^[z]. The filters 16, 17 and 18 model the estimated disturbance noise signal d^[n] such that the filter 17 outputs the inverse of the estimated disturbance noise signal d^[n]. Additionally, the transfer function W[z] is copied (by copying the respective filter coefficients $w_k$) from the filter 17 into the filter 20. The attenuation resulting therefrom is maximum as the error approximates zero (e[n]→0). Therefore, the attenuation is maximum for g=1 as can be seen from FIG. 3. The path including the multiplier 14 and the filter 15 is not active because of 1−g=0 for g=1.

A system as described above with reference to FIG. 2 works well as an ANC system in which a total reduction of noise is desired, which is the case for g=1. However, there are situations in which it may be desirable to only attenuate or boost the noise to a certain extent or to modify the spectral structure of the noise or both. For example, it is not worthwhile to reduce the motor sound of a vehicle to zero since the motor sound provides to the driver important feedback information such as whether the motor is on or off, or an indication of the motor's revolutions per minute (RPM) which may even give a rough impression of the vehicle's speed. Another application may be the so-called vehicle or motor sound tuning, i.e., creating a specific sound, e.g. a more pleasant, sportive or elegant vehicle or motor sound. Thus, it is now assumed that $g \neq 1$.

In the system of FIG. 2, the multiplier 12 is added to the general ANC structure in order to allow such sound tuning. The gain factor g which is multiplied with the compensation signal y[n] by the multiplier 12 corresponds to the overall attenuation of the noise signal x[n] to be achieved. In view of the adaptive filter 11, the multiplier 14 is connected upstream of the filter 21 and compensates for this gain factor g by multiplying the compensation signal y[n] by the quantity 1−g. Thus, the adaptive filter 11 is operated in the same way as it would be with g=1. However, the gain factor g affects the signal e[n] occurring in the listening position 4 as now applies that:

$$E[z]=g\cdot W[z]\cdot S[z]\cdot X[z]+D[z]$$

(instead of $E[z]=W[z]\cdot S[z]\cdot X[z]+D[z]$)

in which $g \neq 1$ and E[z] is the z-Transformation of the corresponding time signal e[n] etc. However, the adaptive filter 11 as part of a control loop still seeks to minimize the error signal e'[n], i.e., e'[n]→0. However, there is an offset in the control loop introduced by gain factor g:

Assuming an ideal model of the secondary path with $\hat{S}[z]=S[z]$ and that the series connection of the transfer functions W[z] and S[z] is matching the transfer function P[z] (W[z]·S[z]=−P[z]), after successful adaption of W[z] (e'[n]→0), a resulting relative attenuation value a can be formed, with:

$$\begin{aligned} Y'[z] &= g\cdot W[z]\cdot S[z]\cdot X[z] \\ &= -g\cdot P[z]\cdot X[z] \\ &= -g\cdot D[z] \end{aligned}$$

$$\begin{aligned} a &= E[z]/D[z] \\ &= (D[z]+Y'[z])/D[z] \\ &= (D[z]-g\cdot D[z])/D[z] \\ &= 1-g \end{aligned}$$

in which E[z], D[z], X[z], Y[z] and Y'[z] represent in the frequency domain the time domain signals e[n], d[n], x[n], y[n] and y[n] frequency domain and g is a real valued gain with $0 \leq g \leq \infty$.

Further assuming that gain factor is g=1 and that the system is operated under real conditions where no infinite attenuation is achievable, a theoretic maximum attenuation factor $a_{max}$ (<1) occurs so that an absolute attenuation a' is the maximum of both values maximum attenuation factor $a_{max}$ and relative attenuation |a|:

$$a'=\max(a_{max}, |a|)$$

For any relative attenuation factor a, in which $$\begin{aligned} a &= E[z]/D[z] \\ &= (D[z]+Y'[z])/D[z] \\ &= (D[z]-g\cdot D[z])/D[z] \\ &= 1-g \end{aligned}$$

and E[z], D[z], X[z], Y[z] and Y'[z] represent in the frequency domain the time domain signals e[n], d[n], x[n], y[n] and y[n] frequency domain, respectively, the following modes of operation may apply:

| | | |
|---|---|---|
| Attenuation: | $0 \leq g \leq 1$ | $a'_{db} = -20\log10(a')$ $a' = \max(a_{max}, \lvert a \rvert)$ |
| Attenuation: | $1 < g \leq 2$ | $a'_{db} = -20\log10(a')$ $a' = \max(a_{max}, \lvert a \rvert)$ |
| Amplification: | $2 < g \leq \infty$ | $a'_{db} = -20\log10(a')$ $a' = \max(a_{max}, \lvert a \rvert)$ |

The attenuation is illustrated either in a linear scale a' (<1) or logarithmic scale $a'_{db}$ (>0).

Figure 3:
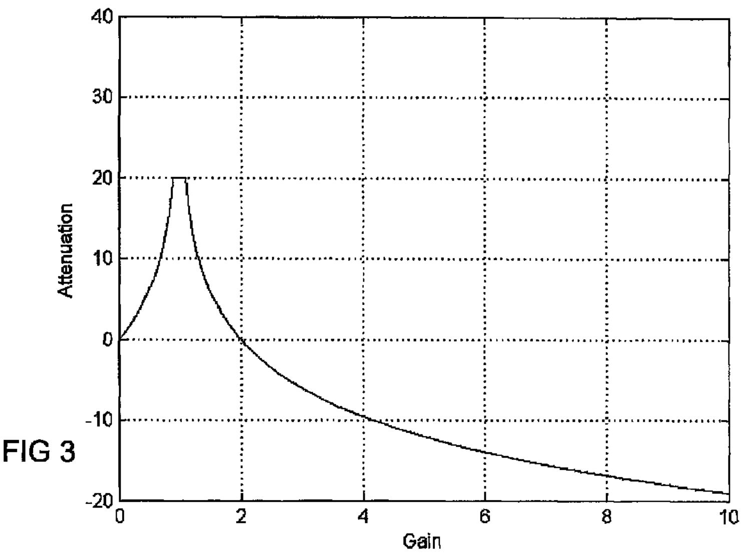
FIG. 3 graphically illustrates the attenuation E[z]/D[z] in dB over gain factor g in the time domain in a system as shown in FIG. 2.
Figure 4:
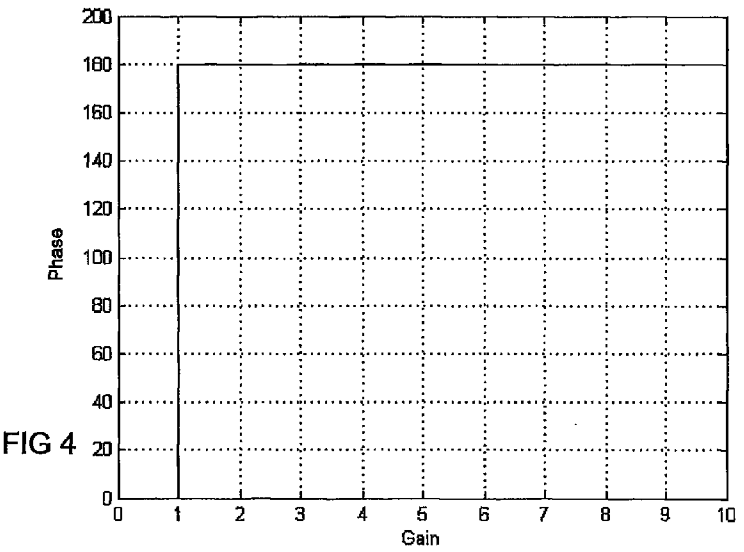
FIG. 4 graphically illustrates the phase of E[z]/D[z] over gain factor g in the time domain in a system as shown in FIG. 2.

FIG. 3 graphically illustrates, by way of example, the attenuation over gain factor g in the system shown in FIG. 2 with a theoretic maximum attenuation factor of $a_{max}=0.1$. FIG. 4 graphically illustrates, also by way of example, the phase of a system as shown in FIG. 2 over gain factor g. As can be seen from FIG. 4, the phase of the attenuation a=1−g is inverted for a gain factor g greater than 1, whereby the phase $\phi_a$ is:

$$\phi_a=\arg\{a\}=a\cdot\tan(Im\{1-g\}/Re\{1-g\})=a\cdot\tan(0)=0,\quad 0\leq g\leq 1$$

$$\phi_a=\arg\{a\}=a\cdot\tan(Im\{1-g\}/Re\{1-g\})=a\cdot\tan(0)+\Pi,\quad 1<g<\infty$$

Figure 5:
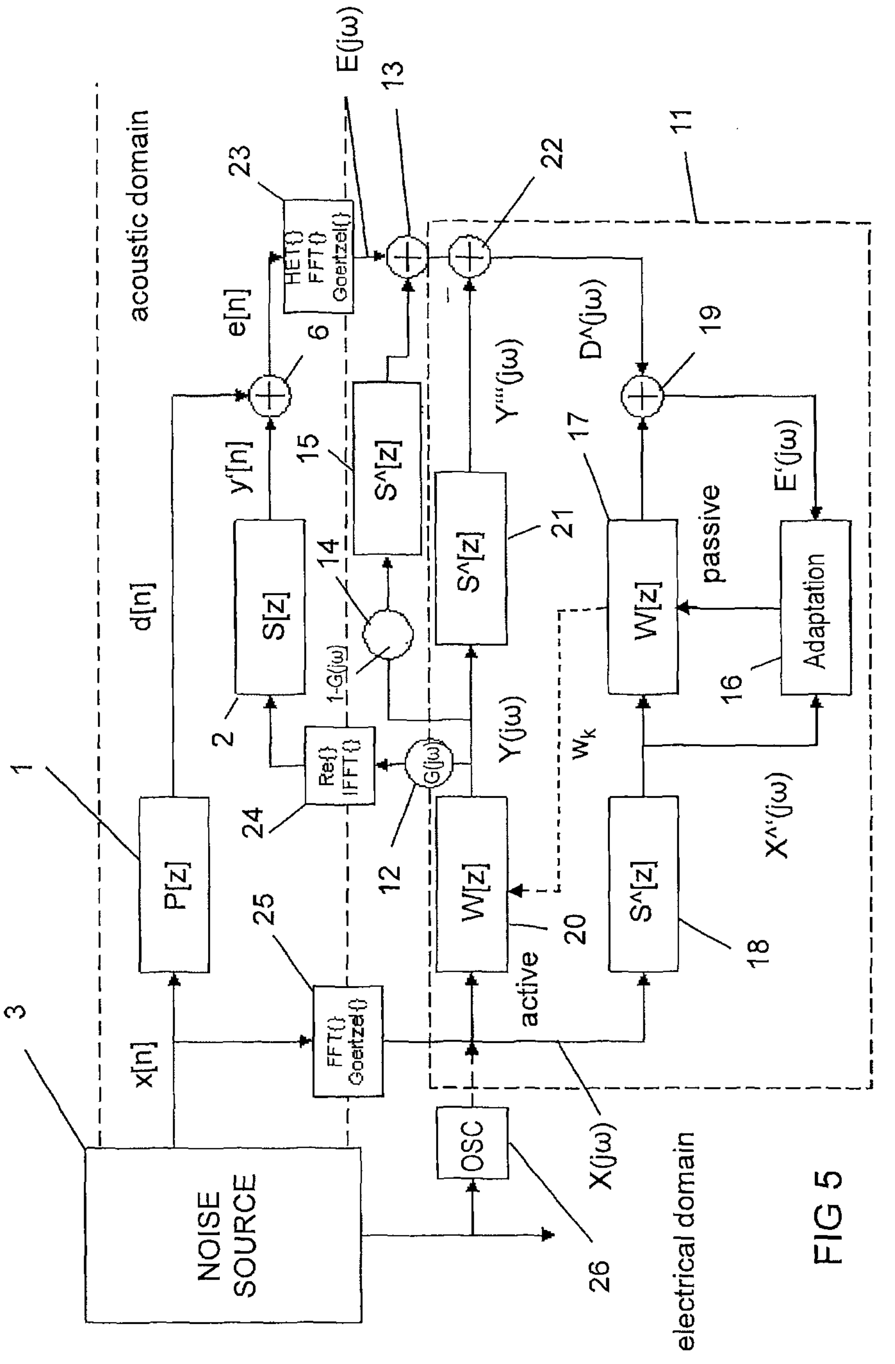
FIG. 5 is a block diagram illustration of an adaptive noise control system as shown in FIG. 2 implemented in the frequency domain and having a frequency dependant complex gain factor G.

FIG. 5 is a block diagram illustration of an adaptive noise control system based on the system shown in FIG. 2 but adapted to have a frequency dependant complex gain factor G(jω) to allow equalization of the noise or spectral sound tuning over frequency, in which now the complex attenuation factor A(jω) is:

$$A(j\omega)=1-G(j\omega)=E(j\omega)/D(j\omega).$$

When using a frequency dependant G, i.e. G(jω), G may be stored as a look-up table in the system, e.g., as a frequency dependant complex array of numbers representing G(jω) in which $\omega_{start}<\omega<\omega_{stop}$ with $\omega_{start}$=start value and $\omega_{stop}$ is the stop value.

In contrast to the system of FIG. 2, in the system of FIG. 5 all signals are not processed in the time domain but in the frequency domain. Accordingly, instead of signals x[n], y[n], e[n], $\hat{y}$'[n], $\hat{d}$[n], $\hat{x}$'[n] and e'[n] in the time domain, signals X(jω), Y(jω), E(jω), $\hat{Y}$'(jω), $\hat{D}$(jω), $\hat{X}$'(jω) and E'(jω) in the frequency domain are used, respectively. The filters 17, 18, 20, 21 and the adaption unit 16 are adapted accordingly in order to exhibit the same behavior as the respective filters in the system of FIG. 2.

As shown in FIG. 5, a calculation unit 23 is connected between the output of the adder 6 and the input of the adder 13, which is designated to receive the error signal e[n] in the system of FIG. 2. A further calculation unit 24 is connected in series with the multiplier 12 and upstream of the secondary path 2. Finally, a still further calculation unit 25 may be connected upstream of the inputs of the filters 18 and 20. Alternatively, an oscillator 26 may be used which is connected upstream of the filters 18 and 20 and which is controlled by the noise source 3, e.g., with a signal representing the revolutions per minute of a motor. The oscillator 26 may be a synthesizer that models the noise generated by the noise source, e.g., on the basis of a signal representing the revolutions per minute of the motor.

A dedicated amplitude and phase characteristic over frequency of the gain factor G(jω) can be implemented, e.g., by a Finite Impulse Response (FIR) filter or an Infinite Impulse Response (IIR) filter or by a look up table in the frequency domain to hold discrete complex values to read out at the specific frequencies ω. As outlined above, the attenuation factor A (jω) is a complex function $A(j\omega)|=|A|\cdot e^{j\Phi A}$ whose absolute value is:

$$|1-G(j\omega)|=|A(j\omega)|,$$

and whose phase is:

$$\arg\{A(j\omega)\}=\phi_A=\arctan(Im\{A(j\omega)\}/Re\{A(j\omega)\})+k\Pi$$

in which Im{ } is the imaginary part, Re{ } is the real part of the attenuation factor A(jω) and integer k depends on the quadrant in the complex plane of A.

Employing complex rotators for the signal Y(jω), a correcting signal is provided which is Y(jω)·G(jω) and which can be transferred by a real operator Re{Y(jω)·G(jω)} or an inverse FFT back into a (real) signal in the time domain by the calculation unit 24. The correcting path is nevertheless operated with 1−G(jω) in which the frequency variable is the normalized frequency $\omega=2\cdot\pi\cdot(f/f_s)$.

In the system shown in FIG. 5, the error signal e[n] in the time domain is transferred to the frequency domain error signal E(jω) by a Fast Fourier Transform (FFT), a heterodyning (HET) operation or a so-called Goertzel algorithm performed in the calculation unit 23.

Fast Fourier transform is an efficient method to compute the discrete Fourier transform (DFT) and its inverse. There are many distinct FFT algorithms involving a wide range of mathematics, from simple complex-number arithmetic to group theory and number theory. A DFT decomposes a sequence of values into components of different frequencies. This operation is useful in many fields but computing it directly from the definition is often too slow to be practical. An FFT computes the DFT and produces exactly the same result as evaluating the DFT definition directly; the only difference is that an FFT is much faster. Since the inverse DFT is almost the same operation as the DFT, any FFT algorithm can easily be adapted for it. By using FFT, signal processing as shown herein has to be done in block processing. This introduces additional delay in the processing of the signals x[n], y[n] and e[n] and leads to a deteriorated performance of the ANC systems.

An alternative way to transform a time domain signal into frequency domain is to heterodyne it. Heterodyning is the generation of new frequencies by mixing, or multiplying, two periodic signals to place a signal of interest into a useful frequency range. In the present example, the error signal e[n] or the reference noise signal x[n] is multiplied with a complex rotator $X(j\omega)=e^{j\omega}$ such that the frequency of interest is shifted towards 0 Hz and the resulting complex signal E(jω) is used for further processing in the signal processing arrangement 10. This can be done e.g. in the form, $$E(j\omega)=(\cos(\omega\cdot n)+j\cdot\sin(\omega\cdot n))\cdot e[n]$$

in which n is, in this example, a digital time index and ω a specific single frequency position of interest. It should be noted that ω can have any frequency value one wishes.

Possible unwanted noise occurring at other frequencies than 0 Hz is suppressed due to averaging operations of the LMS algorithm performed in the adaption unit 16. The heterodyning operation exhibits in contrast to FFT no signal delaying.

Another way to transform a time domain signal in to a frequency domain signal is the so called Goertzel algorithm. The Goertzel algorithm is a digital signal processing technique for identifying frequency components of a signal. While the general Fast Fourier transform (FFT) algorithm computes evenly across the bandwidth of the incoming signal, the Goertzel algorithm looks at specific, predetermined frequencies.

The reference signal is either provided by the oscillator 26 or the calculation unit 25 which either employs an FFT or Goertzel algorithm in the present example. However, Heterodyning may be used as well. The output of the oscillator 26 can be generated according to $$X(j\omega)=\cos(\omega\cdot n)+j\cdot\sin(\omega\cdot n),$$

in which ω represents the frequency of interest and n a discrete time index.

When using the FFT algorithm, it has to be noted that a block-wise processing of the signals (data) is necessary which may cause additional delays and, accordingly, a slower adaption. In contrast, sample-wise processing may be employed as in the Goertzel algorithm. Another option providing smaller delays is using an oscillator, e.g., in connection with a heterodyne operation which also allows sample-wise processing.

Figure 6:
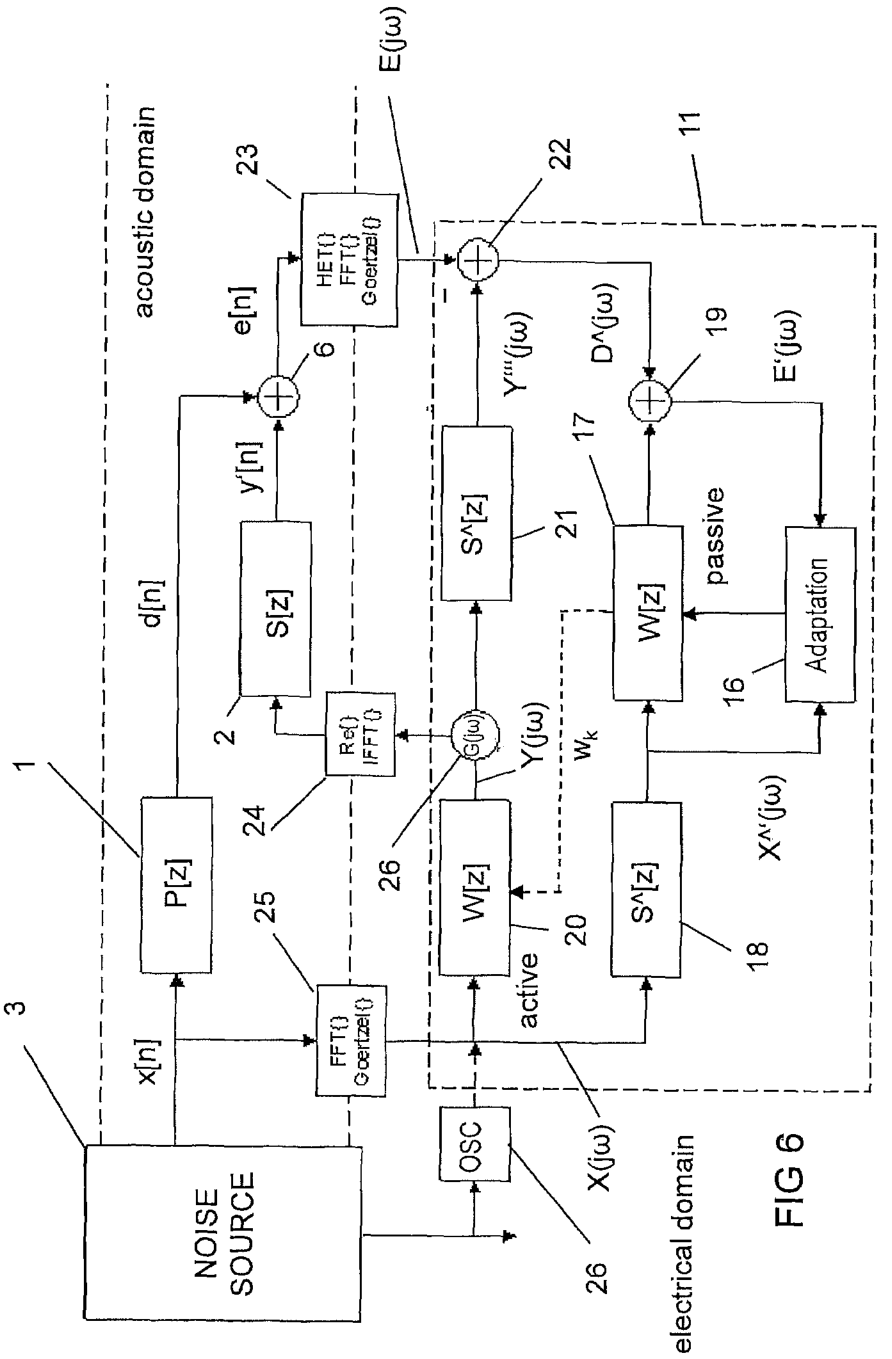
FIG. 6 illustrates an alternative embodiment of the system of FIG. 5.

FIG. 6 illustrates an alternative structure for the system of FIG. 5 in which the multipliers 12 and 14 are substituted by a single multiplier 26 and in which the filter 15 and the adder 13 are omitted. In the system of FIG. 6, signal Y(jω) is multiplied in the multiplying unit 26 with the complex gain G(jω). The output signal of the multiplying unit 26 is supplied to the calculation unit 24 and the filter 21 whose output signal, signal Y'''(jω), is subtracted in the subtractor 22 from the error signal E(jω) provided by the calculation unit 23.

All systems as shown in FIGS. 1-6 have a gain factor in the time or frequency domain which allows to determine the characteristic of attenuation a or $A(j\omega)|=|A|\cdot e^{j\Phi A}$ in advance by a user. A complex filter or look-up table G(jω) stored in a memory of a control system may be used to obtain the desired attenuation A(jω)=1−G(jω). The look-up table is constant and so is the relation E(jω)/D(jω)=A(jω). The acoustic error represented by signal E(jω) is perceived by the listener. The disturbance noise signal D(jω) is the signal which is perceived if the ANC system is switched off. If the user of the system wishes only an attenuation |A(jω)| without phase information to be pre-determined, the look-up table includes only values G(jω)=1−|A(jω)|, with $0\leq G<\infty$ bound to real values. With this setting the phase $\phi_A$ behaves as illustrated above with reference to FIG. 4. If complex values A(jω) are selected, which results, in G(jω)=1−A(jω), then both, amplitude and phase of A(jω) are determined as follows:

$$A(j\omega)=|A(j\omega)|\cdot e^{j\cdot\Phi A}=(|E(j\omega)|/|D(j\omega)|)\cdot e^{j(\Phi E-\Phi D)}$$

Accordingly, the phase of the perceived signal E(jω) relates to the disturbance noise signal D(jω) with $\phi_E=\phi_A+\phi_D$.

A system that overcomes this drawback and that offers a selectable phase $\phi_E$ of the finally perceived error signal E(jω) is described with reference to FIG. 7.

Figure 7:
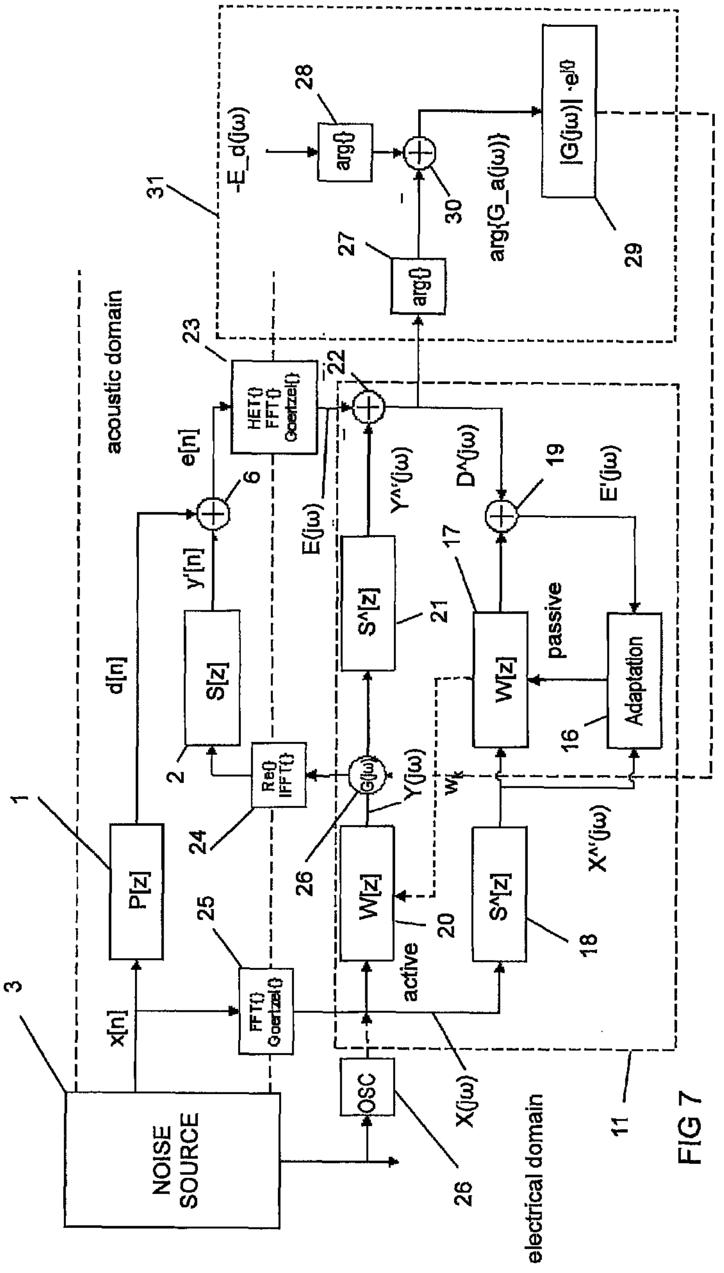
FIG. 7 illustrates a system according to FIG. 6 adapted to automatically adjust the complex gain G over frequency to implement a user selectable attenuation and phase relation of E[z]/D [z]

FIG. 7 illustrates a system according to FIG. 6 with an additional arrangement 31 for automatically adjusting the (complex) gain G(jω) to achieve the above needs. In this arrangement 31, the complex gain G(jω) is provided by a gain control unit which includes three phase calculation units 27, 28, 29 and a subtractor 30. The calculator unit 27 applies the argument function arg{ } on the estimated error signal D^(jω), which is an estimation of the disturbance noise signal d[n] in the frequency domain (=D(jω) at the listening position. The calculation unit 28 applies the argument function arg{ } on a target error signal −E_d(jω). Arg{ } is a function operating on complex numbers (e.g., visualized as a plane), and intuitively gives the angle between the line joining the point to the origin and the positive real axis, known as an argument of the point, that is, the angle between the half-lines of the position vector representing the number and the positive real axis (as outlined in the equation above).

The output signal of the calculator unit 27 is subtracted from the output signal of the calculator unit 28 by the subtractor 30 which supplies a signal arg{G_a(jω)} representing the phase of the newly calculated adaptive gain to the calculator unit 29 where it is processed with an operator $|G(j\omega)|\cdot e^{j\{\ \}}$. Thus, the previous absolute value |G(jω)| is taken again, however the phase $\phi_G$=arg {G(jω)} is newly calculated (i.e., adapted) which is indicated by "{ }". The absolute value |G(jω)| may be stored as a look-up table in the frequency domain. The calculator unit 29 provides the complex gain G(jω) to the multiplier 26. In the arrangement 31, the estimated delayed noise signal D^(jω) is compared with a complex target error signal, i.e., −E_d(jω), and the difference is used by an evaluation arrangement, i.e., the calculator unit 29, to calculate (adapt) the complex gain G(jω) so that, e.g., this difference is kept constant. Thus, the phases of the estimated delayed noise signal D^(jω) and the desired error signal E_d(jω) are compared to each other, i.e., the phase of the estimated disturbance noise signal D^(jω) representing the actual disturbance noise signal d[n] is subtracted from the phase of desired error signal E_d(jω). Based on the difference of the two phases (i.e., the ratio of these two complex signals E_d(jω)/D^(jω)) a new complex gain factor G(jω) is calculated in which only the phase is adapted.

As outlined above, the controllable phase and absolute value of the attenuation A(jω) are related to the error signal E(jω) and the delayed noise signal D(jω) (=d[n] in the frequency domain) according to:

$$A(j\omega)=E(j\omega)/D(j\omega)=1-G(j\omega).$$

As the approximated disturbance noise signal D^(jω) can be estimated by the processing unit 11 (output of the subtractor 22), and if a desired error signal E_d(jω) or its phase arg{E_d(jω)} are readily provided, e.g., by a look up table, the adaptive gain G_a(jω) with $$G\_a(j\omega)=1-A(j\omega)=1-E\_d(j\omega)/D(j\omega)\cong 1-(E\_d(j\omega)/D\hat{\ }(j\omega))$$

or its phase arg{G_a(jω)}

$$\begin{aligned}\arg\{G\_a(j\omega)\} &= \arg\{1-(E\_d(j\omega)/D\hat{\ }(j\omega))\}\\ &= \arg\{-E\_d(j\omega)\}-\arg\{D\hat{\ }(j\omega)\}\end{aligned}$$

can be calculated.

Upon calculation of the phase, in a subsequent step the complex gain used in the system is adapted by discrete calculation according to:

$$G(j\omega,k+1)=|G(j\omega,k)|\cdot e\hat{\ }(j\cdot\arg\{G\_a(j\omega,k)\}$$

$$G(j\omega)=|G(j\omega)|\cdot e\hat{\ }(j\cdot\arg\{G\_a(j\omega)\}.$$

Accordingly, a delay block having a transfer function z^−1 may be connected downstream of the calculation unit 29 (not shown). Also |G(jω)| may be stored in the system as a look-up table. Thus, the phase of the error signal e[n] is changed and controlled such that the sound signal resulting from the superposition of the disturbance noise signal d[n] and the compensation signal y'[n] at the listening position 4 is adapted to the desired characteristic as defined by the target phase of the desired error signal E_d(jω). The sum error signal E(jω) will have a phase $$\phi_{E\_d}=\arg\{E\_d(j\omega)\}$$

and an amplitude $$|E(j\omega)|=|(1-G(j\omega))\cdot D(j\omega)|=|A(j\omega)\cdot D(j\omega)|.$$

Two modes of operation are possible:

1. Only the phase is adapted $$G(j\omega)=|G(j\omega)|\cdot e\hat{\ }(j\cdot\arg\{G\_a(j\omega)\}\text{ or}$$

$$G(j\omega,k+1)=|G(j\omega,k)|\cdot e\hat{\ }(j\cdot\arg\{G\_a(j\omega,k)\}$$

|G(jω)|, E_d(jω) or arg{E_d(jω)} are stored in a look-up table.

2. Amplitude and phase are adapted $$G(j\omega)=G\_a(j\omega)=1-(E\_d(j\omega)/D\hat{\ }(j\omega))\text{ or}$$

$$G(j\omega,k+1)=G\_a(j\omega,k)=1-(E\_d(j\omega)/D\hat{\ }(j\omega,k))$$

Only E_d(jω) is stored in the look-up table and provided acoustically as E(jω).

Figure 8:
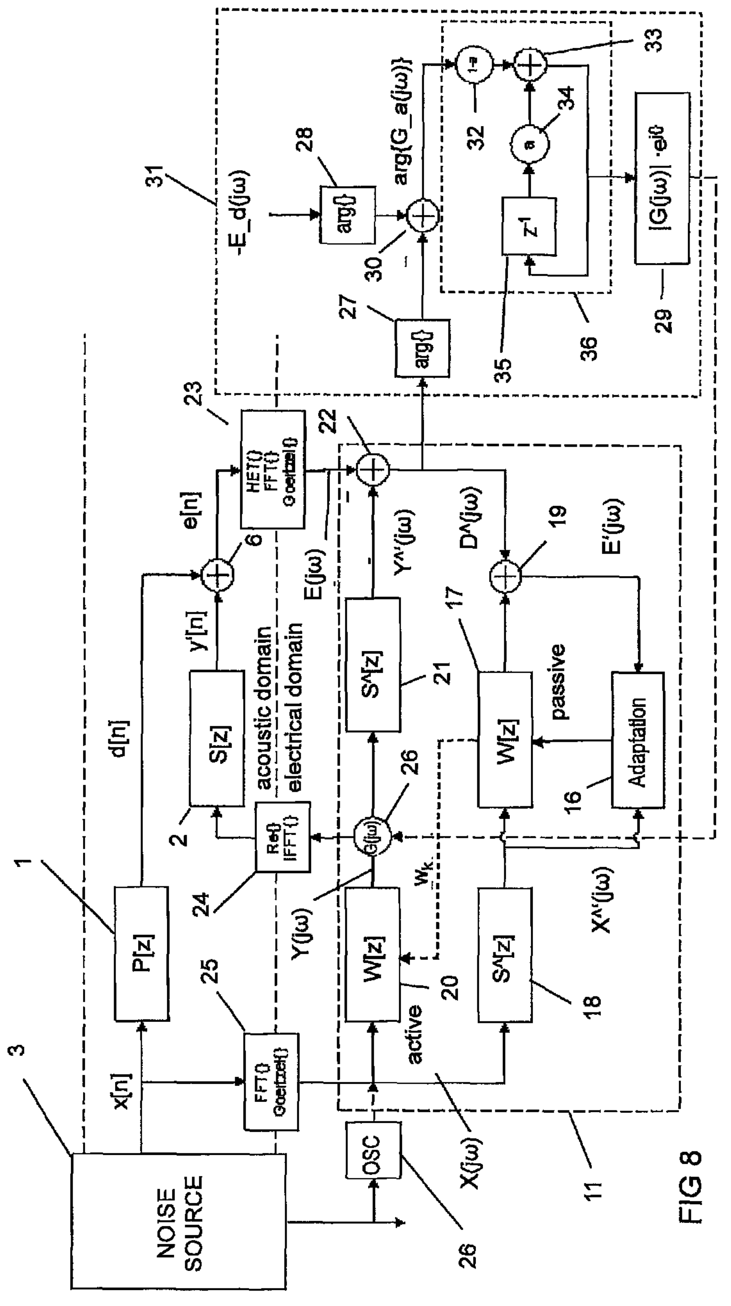
FIG. 8 illustrates a system according to FIG. 7 with additional phase averaging of the adaptive complex gain G.

FIG. 8 illustrates a system according to FIG. 7 with an additional averaging unit 36 connected between the subtractor 30 and the calculator unit 29. The averaging unit 31 includes a coefficient element 32 (with a coefficient 1−a) that is connected between the output of the subtractor 30 and an input of an adder 33 whose other input is connected via a coefficient element 34 (coefficient a) to the output of a latch 35. The input of the latch 35 is connected to the output of the adder 33. Additional units for averaging in the frequency domain, block or sample wise processing, et cetera, may me provided as the case may be (not shown in the FIGS.).

A complex gain and an arrangement for automatically adjusting the complex gain may be used also in connection with systems as illustrated in FIGS. 1, 2 and 5. This arrangement may be included in the adaptive filter (as indicated by dotted line g[z] in FIG. 1). The complex gain factor may also be provided by a controllable filter instead of multipliers or dividers. Furthermore the scope of the invention is not limited to automotive applications, but may also be applied in any other environment (e.g., in consumer applications like home cinema or the like, and also in cinema and concert halls or the like).

In the examples described above, the Modified Filtered X Least Mean Square MFXLMS algorithm may be used as it offers faster convergence since, e.g., with the FXLMS the maximum step size is the reciprocal of the delay occurring in the secondary path. Thus, the convergence delay of the FXLMS algorithm increases with increasing length of the acoustical secondary path in contrast to the MFXLMS. When using the MFXLMS algorithm the copying of the filter coefficients, e.g., from the filter 17 to the filter 20 in the system of FIG. 2, can be controlled thus allowing to keep the system stable if it tends to become instable.

As already mentioned, the reference noise signal x[n] may be an acoustical signal or a non-acoustical (e.g., synthesized) signal. Furthermore, the reference noise signal x[n] may be picked up as an analog signal in the time domain but digitally processed in the frequency domain blockwise (FFT) or samplewise (Goertzel, Heterodyning). The error signal e[n], too, may be picked up as an analog signal in the time domain but digitally processed in the frequency domain blockwise (FFT) or samplewise (Goertzel, Heterodyning). The compensation may be processed blockwise or samplewise in the frequency domain and is radiated acoustically as analog signal in the time domain. The (adaptable) g factor may be processed in the time or frequency domain.

It will be obvious to those reasonably skilled in the art that other components performing the same functions may be suitably substituted. Such modifications to the inventive concept are intended to be covered by the following claims.

What is claimed is:

1. An adaptive noise control system for reducing, at a listening position, the power of an acoustic noise signal radiated from a noise source to the listening position, the system comprising:

an adaptive filter that receives an electrical reference signal in a frequency domain representing the acoustic noise signal and a modified electrical error signal in the frequency domain representing the acoustic signal at the listening position and that provides an electrical output signal;

a signal processing arrangement that receives the electrical output signal and that provides a first electrical compensation signal indicative of the electrical output signal multiplied by a first gain factor and a second electrical compensation signal indicative of the electrical output signal multiplied by a second gain factor and filtered, the second gain factor being equal to 1 subtracted by the first gain factor; the second compensation signal being added to the error signal for compensation;

at least one acoustic transducer that receives the first electrical compensation signal and radiates an acoustic compensation signal indicative of the first electrical compensation signal to the listening position; and a secondary path estimation filter that receives the second electrical compensation signal and provides a filtered signal that is summed with an electrical error signal to provide the modified electrical error signal.

2. The adaptive noise control system of claim 1 in which the gain factor is controllable by an arrangement adapted to automatically adjust the gain factor according to a target noise signal.

3. The adaptive noise control system of claim 2 in which the arrangement for automatically adjusting the complex gain is adapted to compare an estimated noise signal with the target noise signal, to evaluate the difference thereof and to adapt the complex gain.

4. The adaptive noise control system of claim 3 in which the arrangement for automatically adjusting the complex gain is adapted to evaluate the difference of the estimated noise signal and the target noise signal by applying a complex rotator to this difference multiplied with the real value of the complex gain factor.

5. The adaptive noise control system of claim 3 in which the arrangement for automatically adjusting the complex gain is adapted to average the difference of the estimated noise signal and the target noise signal.

6. The adaptive noise control system of claim 3 in which the arrangement for automatically adjusting the complex gain is adapted to compare the argument of the estimated noise signal and the argument of the target noise signal.

7. The adaptive noise control system of claim 3 in which the signal processing arrangement processes at least the error signal in the frequency domain.

8. An adaptive noise control method for reducing, at a listening position, power of an acoustic noise signal radiated from a noise source to the listening position, the method comprising:

providing an electrical reference signal associated with the acoustic noise signal;

filtering the electrical reference signal with an adaptive filter to provide an electrical output signal;

multiplying the electrical output signal by a gain factor to provide a first electrical compensation signal;

multiplying the electrical output signal by a second gain factor to provide a second electrical compensation signal, the second gain factor being equal to 1 subtracted by the first gain factor;

filtering the second electrical compensation signal to provide a modified compensation signal;

radiating a first electrical compensation signal to the listening position with an acoustic transducer;

sensing a residual acoustic error signal at the listening position and providing an electrical error signal indicative thereof;

adding the modified compensation signal to the electrical error signal to provide a compensated error signal; and adapting filter coefficients of the adaptive filter as a function of the compensated error signal.

9. The adaptive noise control method of claim 8 in which the gain factor is controlled by automatically adjusting the gain factor according to a target noise signal.

10. The adaptive noise control method of claim 9 in which an estimated noise signal is compared with the target noise signal, the difference thereof is evaluated and the complex gain is adapted.

11. The adaptive noise control method of claim 10 in which the arrangement for automatically adjusting the complex gain is adapted to evaluate the difference of the estimated noise signal and the target noise signal by applying a complex rotator to this difference multiplied with the real value of the complex gain factor.

12. The adaptive noise control method of claim 10 in which the difference of the estimated noise signal and the target noise signal are averaged.

13. The adaptive noise control method of claim 10 in which the argument of the estimated noise signal and the argument of the target noise signal are compared.

14. The adaptive noise control system of claim 10 in which at least the error signal is processed in the frequency domain.

* * * * *